US007682540B2

(12) United States Patent
Boyan et al.

(10) Patent No.: US 7,682,540 B2
(45) Date of Patent: Mar. 23, 2010

(54) METHOD OF MAKING HYDROGEL IMPLANTS

(75) Inventors: Barbara D. Boyan, Atlanta, GA (US); Stephen J. Kennedy, Alpharetta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 12/117,667

(22) Filed: May 8, 2008

(65) Prior Publication Data
US 2008/0279943 A1    Nov. 13, 2008

Related U.S. Application Data

(63) Continuation of application No. 11/053,410, filed on Feb. 7, 2005.

(60) Provisional application No. 60/542,514, filed on Feb. 6, 2004.

(51) Int. Cl.
*B28B 1/14* (2006.01)
*B29C 39/00* (2006.01)
*B29C 41/00* (2006.01)
*A61F 2/02* (2006.01)
*A61F 2/28* (2006.01)

(52) U.S. Cl. .................. 264/212; 264/214; 264/299; 623/16.11; 623/23.5; 623/23.71; 623/23.72; 623/23.74; 623/23.76

(58) Field of Classification Search ......... 264/1.31–1.34, 264/212–218, 299; 623/1.39–1.4, 16.11–23.63, 623/23.71–23.76
See application file for complete search history.

(56) References Cited

U.S. PATENT DOCUMENTS

| 3,276,996 | A | 10/1966 | Lazare |
| 3,663,470 | A | 5/1972 | Nishimura et al. |
| 3,673,612 | A | 7/1972 | Merrill et al. |
| 3,849,238 | A | 11/1974 | Gould et al. |
| 3,859,421 | A | 1/1975 | Hucke |
| 4,083,906 | A | 4/1978 | Schindler et al. |
| 4,351,069 | A | 9/1982 | Ballintyn et al. |
| 4,472,542 | A | 9/1984 | Nambu |
| 4,517,295 | A | 5/1985 | Bracke et al. |

(Continued)

FOREIGN PATENT DOCUMENTS

DE    20218703    3/2003

(Continued)

OTHER PUBLICATIONS

Andrade et al., "Water as a Biomaterial," Trans. Am. Soc. Artif. Intern. Organs, 19:1 (1973).

(Continued)

*Primary Examiner*—Khanh Nguyen
*Assistant Examiner*—Carson Gross
(74) *Attorney, Agent, or Firm*—Knobbe Martens Olson & Bear, LLP

(57) ABSTRACT

Implantable biomaterials, particularly hydrogel substrates with porous surfaces, and methods for enhancing the compatibility of biomaterials with living tissue, and for causing physical attachment between biomaterials and living tissues are provided. Also provided are implants suitable for load-bearing surfaces in hard tissue repair, replacement, or augmentation, and to methods of their use. One embodiment of the invention relates to an implantable spinal disc prosthesis.

12 Claims, 4 Drawing Sheets

U.S. PATENT DOCUMENTS

| | | | |
|---|---|---|---|
| 4,524,064 A | 6/1985 | Nambu | |
| 4,609,337 A | 9/1986 | Wichterle et al. | |
| 4,663,358 A | 5/1987 | Hyon et al. | |
| 4,664,857 A | 5/1987 | Nambu | |
| 4,693,939 A | 9/1987 | Ofstead | |
| 4,731,081 A | 3/1988 | Tiffany et al. | |
| 4,734,097 A | 3/1988 | Tanabe et al. | |
| 4,753,761 A | 6/1988 | Suzuki | |
| 4,759,766 A | 7/1988 | Buttner-Janz et al. | |
| 4,772,284 A | 9/1988 | Suzuki | |
| 4,784,990 A | 11/1988 | Nimrod et al. | |
| 4,787,905 A | 11/1988 | Loi | |
| 4,808,353 A | 2/1989 | Nambu et al. | |
| 4,851,168 A | 7/1989 | Graiver et al. | |
| 4,911,720 A * | 3/1990 | Collier | 623/23.12 |
| 4,916,170 A | 4/1990 | Nambu | |
| 4,988,761 A | 1/1991 | Ikada et al. | |
| 4,995,882 A | 2/1991 | Destouet et al. | |
| 5,047,055 A | 9/1991 | Bao et al. | |
| 5,095,037 A | 3/1992 | Iwamitsu et al. | |
| 5,106,743 A | 4/1992 | Franzblau et al. | |
| 5,106,876 A | 4/1992 | Kawamura | |
| 5,108,428 A | 4/1992 | Capecchi et al. | |
| 5,108,436 A | 4/1992 | Chu et al. | |
| 5,118,667 A | 6/1992 | Adams et al. | |
| 5,141,973 A | 8/1992 | Kobayashi et al. | |
| 5,171,322 A | 12/1992 | Kenny | |
| 5,171,574 A | 12/1992 | Kuberasampath et al. | |
| 5,192,326 A | 3/1993 | Bao et al. | |
| 5,206,023 A | 4/1993 | Hunziker | |
| 5,219,360 A | 6/1993 | Georgiade | |
| 5,234,456 A | 8/1993 | Silvestrini | |
| 5,244,799 A | 9/1993 | Anderson | |
| 5,258,023 A | 11/1993 | Reger | |
| 5,258,042 A | 11/1993 | Metha | |
| 5,258,043 A | 11/1993 | Stone | |
| 5,260,066 A | 11/1993 | Wood et al. | |
| 5,287,857 A | 2/1994 | Mann | |
| 5,288,503 A | 2/1994 | Wood et al. | |
| 5,290,494 A | 3/1994 | Coombes et al. | |
| 5,314,477 A | 5/1994 | Marnay | |
| 5,314,478 A | 5/1994 | Oka et al. | |
| 5,326,364 A | 7/1994 | Clift, Jr. et al. | |
| 5,336,551 A | 8/1994 | Gravier et al. | |
| 5,336,767 A | 8/1994 | Della Valle et al. | |
| 5,343,877 A | 9/1994 | Park | |
| 5,344,459 A | 9/1994 | Swartz | |
| 5,346,935 A | 9/1994 | Suzuki et al. | |
| 5,397,572 A | 3/1995 | Coombes et al. | |
| 5,399,591 A | 3/1995 | Smith et al. | |
| 5,401,269 A | 3/1995 | Buttner-Janz et al. | |
| 5,409,904 A | 4/1995 | Hecht et al. | |
| 5,410,016 A | 4/1995 | Hubbell et al. | |
| 5,442,053 A | 8/1995 | Della Valle et al. | |
| 5,458,643 A | 10/1995 | Oka et al. | |
| 5,458,645 A | 10/1995 | Bertin | |
| 5,490,962 A | 2/1996 | Cima et al. | |
| 5,492,697 A | 2/1996 | Boyan et al. | |
| 5,494,940 A | 2/1996 | Unger et al. | |
| 5,502,082 A | 3/1996 | Unger et al. | |
| 5,512,475 A | 4/1996 | Naughton et al. | |
| 5,522,898 A | 6/1996 | Bao | |
| 5,534,028 A | 7/1996 | Bao et al. | |
| 5,541,234 A | 7/1996 | Unger et al. | |
| 5,545,229 A | 8/1996 | Parsons et al. | |
| 5,556,429 A | 9/1996 | Felt | |
| 5,556,431 A | 9/1996 | Buttner-Janz | |
| 5,578,217 A | 11/1996 | Unger et al. | |
| 5,626,861 A | 5/1997 | Laurencin et al. | |
| 5,645,592 A | 7/1997 | Nicolais et al. | |
| 5,656,450 A | 8/1997 | Boyan et al. | |
| 5,658,329 A | 8/1997 | Purkait | |
| 5,674,241 A | 10/1997 | Bley et al. | |
| 5,674,295 A | 10/1997 | Ray et al. | |
| 5,674,296 A | 10/1997 | Bryan et al. | |
| 5,688,459 A | 11/1997 | Mao et al. | |
| 5,700,289 A | 12/1997 | Breitbart et al. | |
| 5,705,780 A | 1/1998 | Bao | |
| 5,716,416 A | 2/1998 | Lin | |
| 5,750,585 A | 5/1998 | Park et al. | |
| 5,766,618 A | 6/1998 | Laurencin et al. | |
| 5,769,897 A | 6/1998 | Harle | |
| 5,789,464 A | 8/1998 | Muller | |
| 5,795,353 A | 8/1998 | Felt | |
| 5,824,093 A | 10/1998 | Ray et al. | |
| 5,824,094 A | 10/1998 | Serhan et al. | |
| 5,844,016 A | 12/1998 | Sawhney et al. | |
| 5,847,046 A | 12/1998 | Jiang et al. | |
| 5,855,610 A | 1/1999 | Vacanti et al. | |
| 5,863,297 A | 1/1999 | Walter et al. | |
| 5,863,551 A | 1/1999 | Woerly | |
| 5,876,452 A * | 3/1999 | Athanasiou et al. | 623/23.72 |
| 5,876,741 A | 3/1999 | Ron | |
| 5,880,216 A | 3/1999 | Tanihara et al. | |
| 5,900,245 A | 5/1999 | Sawhney et al. | |
| 5,916,585 A | 6/1999 | Cook et al. | |
| 5,925,626 A | 7/1999 | Della Valle et al. | |
| 5,944,754 A | 8/1999 | Vacanti | |
| 5,947,844 A * | 9/1999 | Shimosaka et al. | 473/379 |
| 5,948,829 A | 9/1999 | Wallajapet et al. | |
| 5,957,787 A * | 9/1999 | Hwang | 473/379 |
| 5,976,186 A | 11/1999 | Bao et al. | |
| 5,981,826 A | 11/1999 | Ku et al. | |
| 6,001,352 A | 12/1999 | Boyan et al. | |
| 6,027,744 A | 2/2000 | Vacanti et al. | |
| 6,060,534 A | 5/2000 | Ronan et al. | |
| 6,093,205 A | 7/2000 | McLeod et al. | |
| 6,102,954 A | 8/2000 | Albrektsson et al. | |
| 6,103,255 A | 8/2000 | Levene et al. | |
| 6,132,465 A | 10/2000 | Ray et al. | |
| 6,156,067 A | 12/2000 | Bryan et al. | |
| 6,171,610 B1 | 1/2001 | Vacanti et al. | |
| 6,187,329 B1 | 2/2001 | Agrawal et al. | |
| 6,206,927 B1 | 3/2001 | Fell | |
| 6,224,630 B1 | 5/2001 | Bao et al. | |
| 6,231,605 B1 * | 5/2001 | Ku | 623/11.11 |
| 6,255,359 B1 | 7/2001 | Agrawal et al. | |
| 6,264,695 B1 | 7/2001 | Stoy | |
| 6,268,405 B1 * | 7/2001 | Yao et al. | 523/113 |
| 6,271,278 B1 | 8/2001 | Park et al. | |
| 6,280,475 B1 | 8/2001 | Bao et al. | |
| 6,337,198 B1 | 1/2002 | Levene et al. | |
| 6,340,369 B1 | 1/2002 | Ferree | |
| 6,341,952 B2 | 1/2002 | Gaylo et al. | |
| 6,344,058 B1 | 2/2002 | Ferree | |
| 6,355,699 B1 | 3/2002 | Vyakarnam et al. | |
| 6,371,984 B1 | 4/2002 | Van Dyke et al. | |
| 6,376,573 B1 | 4/2002 | White et al. | |
| 6,379,962 B1 | 4/2002 | Holy et al. | |
| 6,383,519 B1 | 5/2002 | Sapieszko et al. | |
| 6,402,784 B1 | 6/2002 | Wardlaw | |
| 6,402,785 B1 | 6/2002 | Zdeblick et al. | |
| 6,419,704 B1 | 7/2002 | Ferree | |
| 6,428,576 B1 | 8/2002 | Haldimann | |
| 6,451,059 B1 | 9/2002 | Janas et al. | |
| 6,472,210 B1 | 10/2002 | Holy et al. | |
| 6,482,234 B1 | 11/2002 | Weber et al. | |
| 6,531,523 B1 | 3/2003 | Davankov et al. | |
| 6,533,818 B1 | 3/2003 | Weber et al. | |
| 6,534,084 B1 | 3/2003 | Vyakarnam et al. | |
| 6,558,421 B1 | 5/2003 | Fell et al. | |
| 6,602,291 B1 | 8/2003 | Ray et al. | |
| 6,607,558 B2 | 8/2003 | Kuras | |
| 6,610,094 B2 | 8/2003 | Husson | |

| | | | | | |
|---|---|---|---|---|---|
| 6,629,997 B2 | 10/2003 | Mansmann | 2003/0220695 A1 | 11/2003 | Sevrain |
| 6,645,248 B2 | 11/2003 | Casutt | 2003/0233150 A1 | 12/2003 | Bourne et al. |
| 6,667,049 B2 | 12/2003 | Janas et al. | 2004/0010048 A1 | 1/2004 | Evans et al. |
| 6,686,437 B2 | 2/2004 | Buchman et al. | 2004/0024465 A1 | 2/2004 | Lambrecht et al. |
| 6,707,558 B2 | 3/2004 | Bennett | 2004/0044412 A1 | 3/2004 | Lambrecht et al. |
| 6,710,126 B1 | 3/2004 | Hirt et al. | 2004/0052867 A1 | 3/2004 | Canham |
| 6,726,721 B2 | 4/2004 | Stoy et al. | 2004/0059425 A1 | 3/2004 | Schmieding |
| 6,733,533 B1 | 5/2004 | Lozier | 2004/0063200 A1 | 4/2004 | Chaikof et al. |
| 6,734,000 B2 | 5/2004 | Chin et al. | 2004/0064195 A1 | 4/2004 | Herr |
| 6,740,118 B2 | 5/2004 | Eisermann et al. | 2004/0073312 A1 | 4/2004 | Eisermann et al. |
| 6,773,713 B2 | 8/2004 | Bonassar et al. | 2004/0092653 A1 | 5/2004 | Ruberti et al. |
| 6,783,546 B2 | 8/2004 | Zucherman et al. | 2004/0117022 A1 | 6/2004 | Marnay et al. |
| 6,800,298 B1 | 10/2004 | Burdick et al. | 2004/0143327 A1 | 7/2004 | Ku |
| 6,802,863 B2 | 10/2004 | Lawson et al. | 2004/0143329 A1 | 7/2004 | Ku |
| 6,827,743 B2 | 12/2004 | Eisermann et al. | 2004/0143333 A1 | 7/2004 | Bain et al. |
| 6,840,960 B2 | 1/2005 | Bubb | 2004/0147016 A1 | 7/2004 | Rowley et al. |
| 6,849,092 B2 | 2/2005 | Van Dyke et al. | 2004/0171143 A1 | 9/2004 | Chin et al. |
| 6,855,743 B1 | 2/2005 | Gvozdic | 2004/0172135 A1 | 9/2004 | Mitchell |
| 6,875,232 B2 | 4/2005 | Nigam | 2004/0220296 A1 | 11/2004 | Lowman et al. |
| 6,875,386 B1 * | 4/2005 | Ward et al. .................. 264/154 | 2004/0220669 A1 | 11/2004 | Studer |
| 6,875,442 B2 | 4/2005 | Holy et al. | 2004/0220670 A1 | 11/2004 | Eisermann et al. |
| 6,878,384 B2 | 4/2005 | Cruise et al. | 2004/0249465 A1 | 12/2004 | Ferree |
| 6,881,228 B2 | 4/2005 | Zdeblick et al. | 2005/0037052 A1 | 2/2005 | Udipi et al. |
| 6,893,466 B2 | 5/2005 | Trieu | 2005/0043733 A1 | 2/2005 | Eisermann et al. |
| 6,923,811 B1 | 8/2005 | Carl et al. | 2005/0043802 A1 | 2/2005 | Eisermann et al. |
| 6,960,617 B2 | 11/2005 | Omidian et al. | 2005/0049706 A1 | 3/2005 | Brodke et al. |
| 6,982,298 B2 | 1/2006 | Calabro et al. | 2005/0055094 A1 | 3/2005 | Kuslich |
| 6,993,406 B1 | 1/2006 | Cesarano, III et al. | 2005/0055099 A1 | 3/2005 | Ku |
| 7,008,635 B1 | 3/2006 | Coury et al. | 2005/0071003 A1 | 3/2005 | Ku |
| 7,012,034 B2 | 3/2006 | Heide et al. | 2005/0074877 A1 | 4/2005 | Mao |
| 7,022,522 B2 | 4/2006 | Guan et al. | 2005/0079200 A1 | 4/2005 | Rathenow et al. |
| 7,048,766 B2 | 5/2006 | Ferree | 2005/0090901 A1 | 4/2005 | Studer |
| 7,052,515 B2 | 5/2006 | Simonson | 2005/0096744 A1 | 5/2005 | Trieu et al. |
| 7,060,097 B2 | 6/2006 | Fraser et al. | 2005/0106255 A1 | 5/2005 | Ku |
| 7,066,958 B2 | 6/2006 | Ferree | 2005/0137677 A1 | 6/2005 | Rush |
| 7,066,960 B1 | 6/2006 | Dickman | 2005/0137707 A1 | 6/2005 | Malek |
| 7,083,649 B2 | 8/2006 | Zucherman et al. | 2005/0143826 A1 | 6/2005 | Zucherman et al. |
| 7,091,191 B2 | 8/2006 | Laredo et al. | 2005/0149196 A1 | 7/2005 | Zucherman et al. |
| 7,156,877 B2 | 1/2007 | Lotz et al. | 2005/0154462 A1 | 7/2005 | Zucherman et al. |
| 7,186,419 B2 | 3/2007 | Petersen | 2005/0154463 A1 | 7/2005 | Trieu |
| 7,201,774 B2 | 4/2007 | Ferree | 2005/0169963 A1 | 8/2005 | Van Dyke et al. |
| 7,201,776 B2 | 4/2007 | Ferree et al. | 2005/0171608 A1 | 8/2005 | Peterman et al. |
| 7,214,245 B1 | 5/2007 | Marcolongo et al. | 2005/0177238 A1 | 8/2005 | Khandkar et al. |
| 7,217,294 B2 | 5/2007 | Kusanagi et al. | 2005/0196452 A1 | 9/2005 | Boyan et al. |
| 7,235,592 B2 | 6/2007 | Muratoglu et al. | 2005/0209704 A1 | 9/2005 | Maspero et al. |
| 7,250,060 B2 | 7/2007 | Trieu | 2005/0216087 A1 | 9/2005 | Zucherman et al. |
| 7,264,634 B2 | 9/2007 | Schmieding | 2005/0228500 A1 | 10/2005 | Kim et al. |
| 7,282,165 B2 | 10/2007 | Williams, III et al. | 2005/0233454 A1 | 10/2005 | Nies et al. |
| 7,291,169 B2 | 11/2007 | Hodorek | 2005/0244449 A1 | 11/2005 | Sayer et al. |
| 7,316,919 B2 | 1/2008 | Childs et al. | 2005/0260178 A1 | 11/2005 | Vandenburgh et al. |
| 7,332,117 B2 | 2/2008 | Higham et al. | 2005/0261682 A1 | 11/2005 | Ferree |
| 7,357,798 B2 | 4/2008 | Sharps et al. | 2005/0273176 A1 | 12/2005 | Ely et al. |
| 7,377,942 B2 | 5/2008 | Berry | 2005/0273178 A1 | 12/2005 | Boyan et al. |
| 2001/0029399 A1 | 10/2001 | Ku | 2005/0277921 A1 | 12/2005 | Eisermann et al. |
| 2001/0038831 A1 | 11/2001 | Park et al. | 2005/0278025 A1 | 12/2005 | Ku et al. |
| 2001/0046488 A1 | 11/2001 | Vandenburgh et al. | 2005/0287187 A1 | 12/2005 | Mansmann |
| 2002/0031500 A1 * | 3/2002 | MacLaughlin et al. ... 424/93.21 | 2006/0002890 A1 | 1/2006 | Hersel et al. |
| 2002/0034646 A1 | 3/2002 | Canham | 2006/0052874 A1 | 3/2006 | Johnson et al. |
| 2002/0072116 A1 | 6/2002 | Bhatia et al. | 2006/0052875 A1 | 3/2006 | Bernero et al. |
| 2002/0140137 A1 | 10/2002 | Sapieszko et al. | 2006/0052878 A1 | 3/2006 | Schmieding |
| 2002/0173855 A1 | 11/2002 | Mansmann | 2006/0058413 A1 | 3/2006 | Leistner et al. |
| 2002/0183845 A1 | 12/2002 | Mansmann | 2006/0064172 A1 | 3/2006 | Trieu |
| 2002/0183848 A1 | 12/2002 | Ray et al. | 2006/0064173 A1 | 3/2006 | Guederian |
| 2002/0187182 A1 | 12/2002 | Kramer et al. | 2006/0083728 A1 | 4/2006 | Kusanagi et al. |
| 2003/0008395 A1 | 1/2003 | Holy et al. | 2006/0100304 A1 | 5/2006 | Vresilovic et al. |
| 2003/0008396 A1 | 1/2003 | Ku | 2006/0121609 A1 | 6/2006 | Yannas et al. |
| 2003/0021823 A1 | 1/2003 | Landers et al. | 2006/0122706 A1 | 6/2006 | Lo |
| 2003/0055505 A1 | 3/2003 | Sicotte et al. | 2006/0136064 A1 | 6/2006 | Sherman |
| 2003/0059463 A1 | 3/2003 | Lahtinen | 2006/0136065 A1 | 6/2006 | Gontarz et al. |
| 2003/0082808 A1 | 5/2003 | Guan et al. | 2006/0200250 A1 | 9/2006 | Ku |
| 2003/0175656 A1 | 9/2003 | Livne et al. | 2006/0206209 A1 | 9/2006 | Cragg et al. |
| 2003/0176922 A1 | 9/2003 | Lawson et al. | 2006/0224244 A1 | 10/2006 | Thomas et al. |
| 2003/0199984 A1 | 10/2003 | Trieu | 2006/0229721 A1 | 10/2006 | Ku |

| | | | | | | |
|---|---|---|---|---|---|---|
| 2006/0235541 | A1 | 10/2006 | Hodorek | 2008/0279943 A1 | 11/2008 | Boyan et al. |
| 2006/0257560 | A1 | 11/2006 | Barone et al. | | | |
| 2006/0259144 | A1 | 11/2006 | Trieu | | | |

FOREIGN PATENT DOCUMENTS

| | | |
|---|---|---|
| EP | 0222404 | 5/1987 |
| EP | 0346129 | 12/1989 |
| EP | 0505634 | 9/1992 |
| EP | 0410010 | 10/1993 |
| EP | 0411105 | 6/1995 |
| EP | 0845480 | 3/1998 |
| EP | 0919209 | 6/1999 |
| EP | 1287796 | 3/2003 |
| EP | 1030697 | 8/2003 |
| EP | 1344538 | 9/2003 |
| EP | 1584338 | 10/2005 |
| EP | 1482996 | 11/2005 |
| EP | 0222407 | 5/2007 |
| GB | 02056882 | 3/1981 |
| GB | 02128501 | 5/1984 |
| JP | 02-184580 | 7/1990 |
| JP | 04053843 | 2/1992 |
| JP | 11035732 | 9/1999 |
| JP | 2005-199054 | 7/2005 |
| JP | 07247365 | 9/2005 |
| JP | 2006-101893 | 4/2006 |
| WO | WO 90/07545 | 7/1990 |
| WO | WO 90/07575 | 7/1990 |
| WO | WO 90/10018 | 9/1990 |
| WO | WO 93/16664 | 9/1993 |
| WO | WO 94/01483 | 1/1994 |
| WO | WO 95/25183 | 9/1995 |
| WO | WO 97/06101 | 2/1997 |
| WO | WO 97/46178 | 12/1997 |
| WO | WO 98/02146 | 1/1998 |
| WO | WO 98/50017 | 12/1998 |
| WO | WO 99/25391 | 5/1999 |
| WO | WO 99/34845 | 7/1999 |
| WO | WO 00/30998 | 6/2000 |
| WO | WO 00/42991 | 7/2000 |
| WO | WO 00/62829 | 10/2000 |
| WO | WO 01/02033 | 1/2001 |
| WO | WO 01/22902 | 4/2001 |
| WO | WO 01/59160 | 8/2001 |
| WO | WO 01/64030 | 9/2001 |
| WO | WO 01/70436 | 9/2001 |
| WO | WO 01/91822 | 12/2001 |
| WO | WO 02/09647 | 2/2002 |
| WO | WO 02/30480 | 4/2002 |
| WO | WO 02/064182 | 8/2002 |
| WO | WO 03/030787 | 4/2003 |
| WO | WO 03/092760 | 11/2003 |
| WO | WO 2004/060554 | 7/2004 |
| WO | WO 2004/101013 | 11/2004 |
| WO | WO 2005/077013 | 8/2005 |
| WO | WO 2005/077304 | 8/2005 |
| WO | WO 2005/097006 | 10/2005 |
| WO | WO 2006/018531 | 2/2006 |
| WO | WO 2006/019634 | 2/2006 |
| WO | WO 2006/030054 | 3/2006 |
| WO | WO 2006/034365 | 3/2006 |

| | | | |
|---|---|---|---|
| 2006/0282165 | A1 | 12/2006 | Pisharodi |
| 2006/0282166 | A1 | 12/2006 | Molz et al. |
| 2006/0287730 | A1 | 12/2006 | Segal et al. |
| 2006/0293561 | A1 | 12/2006 | Abay |
| 2006/0293751 | A1 | 12/2006 | Lotz et al. |
| 2007/0010889 | A1 | 1/2007 | Francis |
| 2007/0014867 | A1 | 1/2007 | Kusanagi et al. |
| 2007/0032873 | A1 | 2/2007 | Pisharodi |
| 2007/0038301 | A1 | 2/2007 | Hudgins |
| 2007/0043441 | A1 | 2/2007 | Pisharodi |
| 2007/0067036 | A1 | 3/2007 | Hudgins et al. |
| 2007/0073402 | A1 | 3/2007 | Vresilovic et al. |
| 2007/0093906 | A1 | 4/2007 | Hudgins et al. |
| 2007/0106387 | A1 | 5/2007 | Marcolongo et al. |
| 2007/0116678 | A1 | 5/2007 | Sung et al. |
| 2007/0118218 | A1 | 5/2007 | Hooper |
| 2007/0118225 | A1 | 5/2007 | Hestad et al. |
| 2007/0134333 | A1 | 6/2007 | Thomas et al. |
| 2007/0135922 | A1 | 6/2007 | Trieu |
| 2007/0142326 | A1 | 6/2007 | Shue |
| 2007/0162135 | A1 | 7/2007 | Segal et al. |
| 2007/0164464 | A1 | 7/2007 | Ku |
| 2007/0167541 | A1 | 7/2007 | Ruberti et al. |
| 2007/0168039 | A1 | 7/2007 | Trieu |
| 2007/0173951 | A1 | 7/2007 | Wijlaars et al. |
| 2007/0179606 | A1 | 8/2007 | Huyghe et al. |
| 2007/0179614 | A1 | 8/2007 | Heinz et al. |
| 2007/0179615 | A1 | 8/2007 | Heinz et al. |
| 2007/0179617 | A1 | 8/2007 | Brown et al. |
| 2007/0179618 | A1 | 8/2007 | Trieu et al. |
| 2007/0179620 | A1 | 8/2007 | Seaton, Jr. et al. |
| 2007/0179621 | A1 | 8/2007 | McClellan, III et al. |
| 2007/0179622 | A1 | 8/2007 | Denoziere et al. |
| 2007/0196454 | A1 | 8/2007 | Stockman et al. |
| 2007/0202074 | A1 | 8/2007 | Shalaby |
| 2007/0203095 | A1 | 8/2007 | Sadozai et al. |
| 2007/0203580 | A1 | 8/2007 | Yeh |
| 2007/0208426 | A1 | 9/2007 | Trieu |
| 2007/0213718 | A1 | 9/2007 | Trieu |
| 2007/0213822 | A1 | 9/2007 | Trieu |
| 2007/0213823 | A1 | 9/2007 | Trieu |
| 2007/0213824 | A1 | 9/2007 | Trieu |
| 2007/0213825 | A1 | 9/2007 | Thramann |
| 2007/0224238 | A1 | 9/2007 | Mansmann et al. |
| 2007/0225823 | A1 | 9/2007 | Hawkins et al. |
| 2007/0227547 | A1 | 10/2007 | Trieu |
| 2007/0233259 | A1 | 10/2007 | Muhanna et al. |
| 2007/0265626 | A1 | 11/2007 | Seme |
| 2007/0270970 | A1 | 11/2007 | Trieu |
| 2007/0270971 | A1 | 11/2007 | Trieu et al. |
| 2007/0299540 | A1 | 12/2007 | Ku |
| 2008/0004707 | A1 | 1/2008 | Cragg et al. |
| 2008/0015697 | A1 | 1/2008 | McLeod et al. |
| 2008/0021563 | A1 | 1/2008 | Chudzik |
| 2008/0031962 | A1 | 2/2008 | Boyan et al. |
| 2008/0045949 | A1 | 2/2008 | Hunt et al. |
| 2008/0051889 | A1 | 2/2008 | Hodorek |
| 2008/0057128 | A1 | 3/2008 | Li et al. |
| 2008/0075657 | A1 | 3/2008 | Abrahams et al. |
| 2008/0077242 | A1 | 3/2008 | Reo et al. |
| 2008/0077244 | A1 | 3/2008 | Robinson |
| 2008/0103599 | A1 | 5/2008 | Kim et al. |
| 2008/0114367 | A1 | 5/2008 | Meyer |
| 2008/0125870 | A1 | 5/2008 | Carmichael et al. |
| 2008/0131425 | A1 | 6/2008 | Garcia et al. |
| 2008/0145404 | A1 | 6/2008 | Hill et al. |
| 2008/0166329 | A1 | 7/2008 | Sung et al. |
| 2008/0279941 | A1 | 11/2008 | Boyan et al. |

OTHER PUBLICATIONS

Ariga et al., "Immobilization of Microorganisms with PVA Hardened by Iterative Freezing and Thawing," Journal of Fermentation Technology, 65(6): pp. 651-658 (1987).

Boyan et al., "Effect of Titanium Surface Characteristics on Chondrocytes and Osteoblasts in Vitro," Cells and Materials, vol. 5, No. 4, pp. 323-335 (1995).

Boyan et al., "Osteoblast-Mediated Mineral Deposition in Culture is Dependent on Surface Microtopography," Calcif. Tissue Int., 71:519-529 (2002).

Brunette, "The Effects of Implant Surface Topography on the Behavior of Cells," Int. J. Oral Maxillofac Implants, 3:231-246 (1988).

Chen et al., "Boundary layer infusion of heparin prevents thrombosis and reduces neointimal hyperplasia in venous polytetrafluoroethylene grafts without system anticoagulation," J. Vascular Surgery, 22:237-247 (1995).

Chu et al., "Polyvinyl Alcohol Cryogel: An Ideal Phantom Material for MR Studies of Arterial Elasticity," Magnetic Resonance in Medicine, v. 37, pp. 314-319 (1997).

Hickey et al., "Mesh size and diffusive characteristics of semicrystalline poly(vinyl alcohol) membranes prepared by freezing/thawing techniques," Journal of Membrane Science, 107(3), pp. 229-237 (1995).

Hoffman et al., "Interactions of Blood and Blood Components at Hydrogel Interfaces," Ann. New York Acad. Sci., 283:372-382 (1977).

International Search Report for Application No. PCT/US2005/03899 mailed Jul. 15, 2008 (PCT/US2005/03899 is the corresponding PCT application of U.S. Appl. No. 11/053,410).

International Search Report for Application No. PCT/US2005/004045 mailed Jul. 15, 2005 (PCT/US2005/004045 is the corresponding PCT application of U.S. Appl. No. 11/053,409).

Kieswetter et al., "The Role of Implant Surface Characteristics in the Healing of Bone," Crit. Rev. Oral Biol. Med., 7(4):329-345 (1996).

Kieswetter et al., "Surface roughness modulates the local production of growth factors and cytokines by osteoblast-like MG-63 cells," Journal of Biomedical Materials Research, vol. 32, pp. 55-63 (1996).

Kohavi et al., "Markers of primary mineralization are correlated with bone-bonding ability of titanium or stainless steel in vivo," Clin. Oral. Impl. Res., 6:1-13 (1995).

Koutsopoulos et al., "Calcification of porcine and human cardiac valves: testing of various inhibitors for antimineralization," J. Mater. Sci. Mater. Med., 9:421-424 (1998).

Landolt et al., "Electrochemical micromachining, polishing and surface structuring of metals: fundamental aspects and new developments", Elsevier Science Ltd. (2003).

Lazzeri et al., "Physico-chemical and mechanical characterization of hydrogels of poly(vinyl alcohol) and hyaluronic acid," J. Mater. Sci. In Med., 5:852-867 (1994).

Liao et al., "Response of rat osteoblast-like cells to microstructured model surfaces in vitro," Biomaterials, 24, pp. 649-654 (2003).

Lozinsky et al., "Study of cryostructurization of polymer systems. VII. Structure formation under freezing of poly(vinyl alcohol) acqueous solutions," Colloid & Polymer Science, vol. 264, pp. 19-24 (1986).

Lozinsky et al., "Poly(vinyl alcohol) cryogels employed as matrices for cell immobilization. 2. Entrapped cells resemble porous fillers in their effects on the properties of PVA-cryogel carrier," Enzyme and Microbial Technology, vol. 20, No. 3, pp. 182-192 (1997).

Lozinsky et al., "Poly(vinyl alcohol) cryogels employed as matrices for cell immobilization. 3. Overview of recent research and developments," Enzyme and Microbial Technology, vol. 23, No. 3-4, pp. 227-242 (1998).

Lozinsky et al., "Study of Cryostructuration of Polymer Systems. XI. The Formation of PVA Cryogels by Freezing-Thawing the Polymer Aqueous Solutions Containing Additives of Some Polyols," Journal of Applied Polymer Science, vol. 58, pp. 171-177 (1995).

Lozinsky et al., "Study of Cryostructuration of Polymer Systems. XII. Poly(vinyl alcohol) Cryogels: Influence of Low-Molecular Electrolytes," Journal of Applied Polymer Science, vol. 61, pp. 1991-1998 (1986).

Lusta et al., "Immobilization of fungus *Aspergillus* sp. by a novel cryogel technique for production of extracellular hydrolytic enzymes", Process Biochemistry, vol. 35, pp. 1177-1182 (2000).

Martin et al., "Effect of titanium surface roughness on proliferation, differentiation, and protein synthesis of human osteoblast-like cells (MG63)," Journal of Biomedical Materials Research, vol. 29, pp. 389-401 (1995).

Nagura et al., "Structure of poly(vinyl alcohol) hydrogel prepared by repeated freezing and melting," Polymer, 30:762-765 (1989).

Oka et al., "Development of an Artificial Articular Cartilage", Clinical Materials, vol. 6, pp. 361-381 (1990).

Ong et al., "Osteoblast Responses to BMP-2-Treated Titanium In Vitro," The International Journal of Oral & Maxillofacial Implants, vol. 12, No. 5, pp. 649-654 (1997).

Peppas et al., "Structure of Hydrogels by Freezing-Thawing Cyclic Processing," Bulletin of the American Physical Society, 36:582 (1991).

Peppas et al., "Ultrapure poly(vinyl alcohol) hydrogels with mucoadhesive drug delivery characteristics," European Journal of Pharmaceutics and Biopharmaceutics, 43(1): 51-58 (1997).

Peppas et al., "Reinforced uncrosslinked poly(vinyl alcohol) gels produced by cyclic freezing-thawing processes: a short review," Journal of Controlled Release, 16(3): 305-310 (1991).

Peppas et al., "Controlled release from poly(vinyl alcohol) gels prepared by freezing-thawing processes," Journal of Controlled Release, vol. 18, pp. 95-100 (1992).

Ratner et al., Biomaterials Science An Introduction to Materials in Medicine, Academic Press, pp. 52, 53, & 62 (1996).

Schwartz et al., "Underlying Mechanisms at the Bone-Biomaterial Interface," Journal of Cellular Biochemistry, 56:340-347 (1994).

Singh et al., "Polymeric Hydrogels: Preparation and Biomedical Applications," J. Sci. Ind. Res., 39:162 (1980).

Stauffer et al., "Poly(vinyl alcohol) hydrogels prepared by freezing-thawing cyclic processing," Polymer 33(1818):3932-3936 (1992).

Stewart, J.E. et al., "Protein release from PVA gels prepared by freezing and thawing techniques," Proc. Int. Symp. Controlled Release Bioact. Mater., $26^{th}$, 1004-1005 (1999).

Szczesna-Antezak et al., "*Bacillus subtilis* cells immobilised in PVA-cryogels," Biomolecular Engineering, vol. 17, pp. 55-63 (2001).

The American Heritage® Science Dictionary [online], Houghton Mifflin Company, 2002 [retrieved on Jun. 3, 2008]. Retrieved from the internet: <URL: http://dictionary.reference.com/browse/pore>.

Watase et al., "Rheological and DSC Changes in Poly(vinyl alcohol) Gels Induced by Immersion in Water," Journal of Polymer Science, Polym. Phys. Ed, 23(9): 1803-1811 (1985).

Watase et al., "Thermal and rheological properties of poly(vinyl alcohol) hydrogels prepared by repeated cycles of freezing and thawing," Makromol. Chem., v. 189, pp. 871-880 (1988).

Wilcox et al., "Microstructure of Poly(vinyl alcohol) Hydrogels Produced by Freeze/Thaw Cycling," Journal of Polymer Sciences: Part B: Polymer Physics, vol. 37, pp. 3438-3454 (1999).

WordNet® 3.0 [online], Princeton University, 2006 [retrieved on Aug. 6, 2008]. Retrieved from the Internet: <URL: http://dictionary.reference.com/browse/mesh>.

Yamaura et al., "Properties of Gels Obtained by Freezing/Thawing of Poly(vinyl Alcohol)/Water/Dimethyl Sulfoxide Solutions," J. Appl. Polymer Sci., 37:2709-2718 (1989).

Yokoyama et al., "Morphology and structure of highly elastic poly(vinyl alcohol) hydrogel prepared by repeated freezing-and-melting", Colloid & Polymer Science, vol. 264, No. 7, pp. 595-601 (1986).

Zheng-Qiu et al., "The development of artificial articular cartilage—PVA-hydrogel," Bio-Medical Materials and Engineering, vol. 8, pp. 75-81 (1998).

* cited by examiner

Top View

Front View

Section A-A

METHOD OF MAKING HYDROGEL IMPLANTS

CROSS REFERENCE TO RELATED APPLICATIONS

This application is a continuation of U.S. patent application Ser. No. 11/053,410, filed Feb. 7, 2005, which claims the benefit of U.S. Provisional Patent Application Ser. No. 60/542,514, filed Feb. 6, 2004, both of which are incorporated by reference herein in their entireties.

BACKGROUND OF THE INVENTION

1. Field of the Invention

The present invention relates to the use of surface modified biocompatible materials to promote the attachment of bone or bone-like cells to an implant surface. The surface of the biomaterials, which may include hydrogels, when modified in accordance with the description herein, directs the cells that migrate to the implant site to differentiate into cells that attach and lay down bone or bone-derivative material, or cartilage or cartilaginous material further enhancing the biocompatibility of the implanted device.

2. Background Art

Materials used in the construction of implantable medical devices must be nontoxic, nonantigenic, and noninflammatory. Hydrogels are a preferred type of polymeric material for implantable devices. Because of their high water content, analogous to living tissue, they are superior in biocompatibility to non-hydrous polymeric materials.

U.S. Pat. No. 5,981,826, issued to Ku et al., describes the preparation of polyvinyl alcohol hydrogels (PVA-H) by physically crosslinking an aqueous solution of polyvinyl alcohol (PVA) to produce a gel. The crosslinking is accomplished by subjecting the aqueous PVA solution to multiple cycles of freezing and thawing. One limitation of the prior art is that the hydrogels produced are relatively nonporous and the pore size and degree of porosity, that is the density of the pores within the hydrogel, cannot vary independently of the mechanical properties or stiffness of the hydrogel.

Methods for producing certain porous hydrogels also exist in the art. U.S. Pat. No. 6,268,405 issued to Yao et al., describes methods for creating porous PVA-Hs by including immiscible materials in the polymerization process. After the hydrogel is polymerized, the included immiscible materials are washed out of the hydrogel by an appropriate solvent, yielding pores which are broadly distributed throughout the hydrogel. Controlling the size and density of the pores is accomplished by varying the molecular weight of the immiscible materials. A disadvantage of Yao et al. is that the range of attainable pore sizes is limited. Moreover, the invention of Yao et al. is limited in that it can only produce hydrogels whose pores extend throughout the hydrogel. The pores in Yao et al. are intended to create vascularization of the hydrogel in soft or non-load bearing tissue. A further disadvantage of Yao et al. is that the pore sizes are broadly distributed about the average pore size.

In addition to crosslinking by physical means, hydrogels may be chemically crosslinked using, for example, methods similar to those described by Müller in U.S. Pat. No. 5,789,464. Similarly, chemical crosslinking or polymerization methods may also be used to adhere hydrogels to surfaces, including biological tissues. U.S. Pat. No. 5,900,245, issued to Sawhney et al., describes applications of these techniques. These and other methods for the crosslinking or further polymerization of hydrogels are derived from methods used in the polymer industry and are well known in the art.

Artificial discs intended for the replacement of a damaged intravertebral disc have been described. These are typically articulated devices comprising two rigid metal plates adhered to opposite ends of an elastomeric core. In use, the artificial disc is placed in the intervertebral space and the metal plates are secured to the surfaces of adjacent vertebrae. Various embodiments of artificial discs of this type are described in U.S. Pat. Nos. 5,674,296 and 6,156,067, issued to Bryan et al., U.S. Pat. No. 5,824,094, issued to Serhan et al., U.S. Pat. No. 6,402,785, issued to Zdeblick et al. More recent embodiments, e.g. U.S. Pat. No. 6,419,704, issued to Ferree and U.S. Pat. No. 6,482,234, issued to Weber et al., include descriptions of elastomeric cores that may be formed from materials with different elasticities to better mimic the native structure of spinal discs.

The disadvantages of the artificial disc devices of the prior art are numerous. These prior art devices require the mechanical attachment of rigid artificial materials, such as titanium, directly to the bone with screws, staples, nails, cement, or other mechanical means. These rigid materials are only minimally compatible with natural, living bone and separation of the implant from the bone is often observed over long-term implantation. In addition, materials used in artificial discs of the prior art have physical and mechanical properties distinctly different from those of natural spinal, discs and thus, inadequately duplicate the desired properties of native spinal discs.

Vertebral fusion is still the most commonly performed procedure to treat debilitating pain associated with degenerative spinal disc disease or disc trauma, despite the fact that the procedure has many drawbacks. Vertebral fusion increases stress and strain on the discs adjacent to the fusion site, and it is now widely accepted that fusion is responsible for the accelerated degeneration of adjacent levels. Current multi-component spinal disc prosthesis designs, elastomeric cores with metal plates on both the upper and lower surfaces, are susceptible to problems with interfacial bonding and wear. These designs have shown spontaneous device detachment due to retraction of bone tissue from the metal surface.

Bone ingrowth and attachment in the art has often required the use of bone promoting growth factors. For example, U.S. Pat. No. 5,108,436, issued to Chu et al., describes using a porous implant for use in load bearing bone replacement which is used in combination with an osteogenic factor such as TGF-$\beta$.

Biomedical devices which are implanted in or around bone often fail because of fibrinogen encapsulation of the implant instead of cellular attachment to the implant itself. This encapsulation is a defensive reaction attempting to minimize contact between the body and the implant and is considered a sign of implant incompatibility.

Moreover, the art of bone ingrowth to implantable surface contains a multitude of examples relating to porous directed ingrowth where bone essentially grows into and around channels of the implant. For example, U.S. Pat. No. 4,911,720, issued to Collier et al., discusses the ingrowth of bone into interconnecting pores which essentially locks bone into place. This method is disadvantageous in that bone does not actually attach to the material, instead bone attaches to other bone around the implant. In the unfortunate event that an implant must be removed, this type of Collier ingrowth results in large amounts of disruption to the surrounding bone tissue.

The present invention describes a biomaterial for implantation into the body. The biomaterial, which can be a hydrogel, possesses a textured surface which is comprised of superficial surface pores. As used herein, the term pores shall include cavities, indentations, holes and openings. Stated differently, the pores on the surface of the hydrogel substrate do not extend throughout the hydrogel but instead remain within a region near the surface. The hydrogel substrate can be comprised of two or more pore sizes. Specifically, the pores of the first size each have a diameter of between 3 and 1000 micrometers, preferably between 10 and 300 micrometers, and preferably between 30 and 100 micrometers. Further, the pores of the second size would each have a diameter of between 0.5 to 20 micrometers, preferably between 1 to 10 micrometers, and preferably between 2 and 5 micrometers. One embodiment of the present invention provides the second, smaller pores disposed within the first, larger pores. The superficial pores of the present invention extend into the hydrogel substrate less than 1 millimeter, preferably 500 micrometers, and preferably 200 micrometers, from the surface. The hydrogel substrate of the present embodiment can comprise polyvinyl alcohol having a water content of at least 5% and preferably at least 30%.

The present invention is also drawn to a hydrogel substrate comprising a hydrogel surface having thereon a plurality of first substantially uniform superficial pores and a unique plurality of second substantially uniform superficial pores. This hydrogel can possess two different yet substantially uniform superficial pore sizes grouped into a first, larger pore size and a second, smaller pore size. The pores of one size are substantially uniform in diameter relative to the other pores of the same size. Specifically, the first pores have an average diameter of between 2 and 600 micrometers, preferably between 5 and 200 micrometers, and preferably between 20 and 60 micrometers. Further, the second pores have an average diameter of between 0.1 and 10 micrometers, preferably between 0.2 to 5 micrometers, and preferably between 0.5 to 2 micrometers. The superficial pores of the present invention can be arranged so that the smaller, second pores are within the larger, first pores. The superficial pores of the present invention extend into the hydrogel substrate less than 1 millimeter, preferably no more than 500 micrometers, and preferably no more than 200 micrometers. The hydrogel substrate of the present embodiment can be made up of polyvinyl alcohol having a water content of at least 5% and preferably at least 30% w/w of the overall hydrogel.

DETAILED DESCRIPTION OF THE INVENTION

Figure 1:
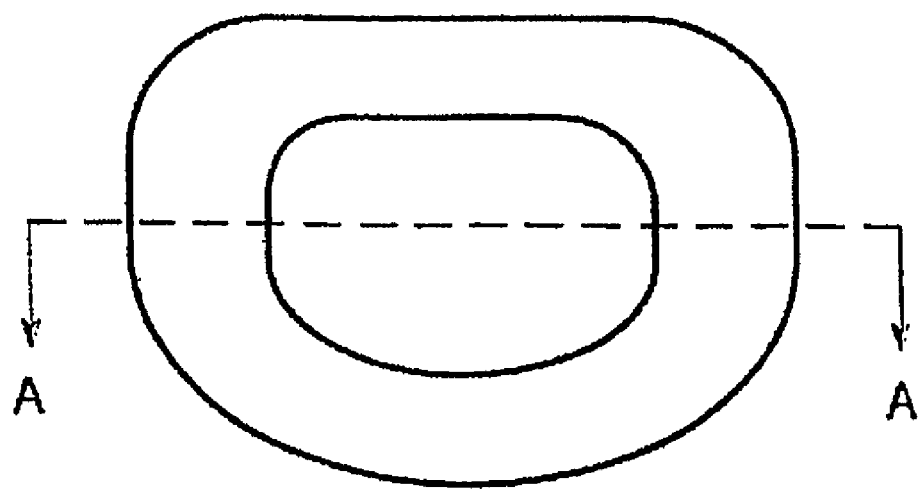
FIG. 1 is a spinal disc replacement device made in accordance with one embodiment of the present invention.
Figure 1:
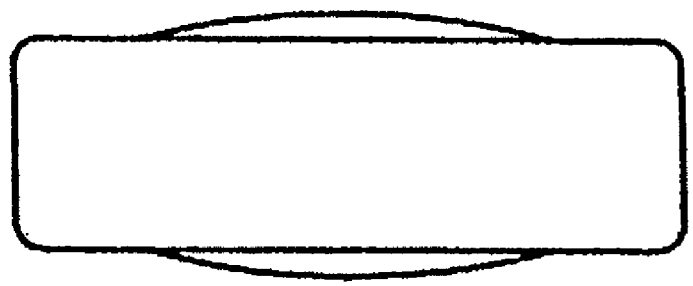
Figure 1:
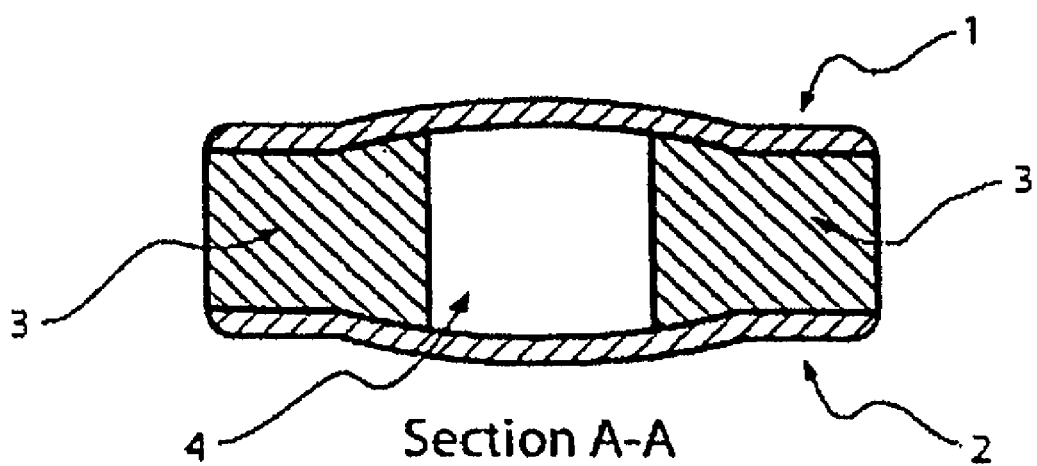

The present invention is drawn to a biomaterial substrate which may comprise a hydrogel surface having thereon a plurality of first substantially uniform superficial pores and a unique plurality of second substantially uniform superficial pores. Specifically, the pores of the first size preferably each have a diameter of between 3 and 1000 micrometers, preferably between 10 and 300 micrometers, and preferably between 30 and 100 micrometers, including without limitation, pores with a cross-section of 30, 40, 50, 60, 70, 80, 90, and 100 micrometers. Further, the pores of the second size preferably each have a diameter of between 0.5 to 20 micrometers, preferably between 1 to 10 micrometers, and preferably between 2 and 5 micrometers, including without limitation, pores with a cross-section of 0.5, 1, 2, 3, 4, 5, 6, 7, 8, 9, 10, 11, 12, 13, 14, 15, 16, 17, 18, 19, and 20 micrometers. It should be readily apparent to one of ordinary skill in the art that the use of the term diameter also would encompass the cross-section of the pore when not a perfect circle. In fact, the term "pore" should not be read to be limited to circular or spherical shapes. Squares, polygons, triangles, octagons, quadrahedrens, or any other geometric or amorphic structure would perform the function for the invention if properly positioned and sized. One embodiment of the present invention provides the second, smaller pores within the first, larger pores. The invention provides that third, fourth, fifth, and greater substantially uniform pore sizes can be on the hydrogel surface. By substantially uniform it is meant that the pore sizes of a particular class (e.g., first, second, etc.) do not vary more than 10%, preferably the pore sizes of a particular class vary less than 5%, 4%, 3%, more preferably less than 2%, and preferably less than 1% or 0.5%.

The superficial pores of the present invention would extend into the hydrogel substrate no more than 1 millimeter, preferably 500 micrometers, and preferably 200 micrometers, from the surface. The hydrogel substrate of the present embodiment can comprise polyvinyl alcohol having a water content of at least 5% and preferably at least 30% w/w of the overall hydrogel.

The present invention is also drawn to a hydrogel substrate comprising a hydrogel surface having thereon a plurality of first substantially uniform superficial pores and a unique plurality of second substantially uniform superficial pores. This hydrogel substrate can possess two different yet substantially uniform superficial pore sizes grouped into a first, larger pore size and a second, smaller pore size. The pores of one size are substantially uniform in diameter relative to the other pores of the same size. Specifically, the first pores have an average diameter of between 2 and 600 micrometers, preferably between 5 and 200 micrometers, and preferably between 20 and 60 micrometers. Further, the second pores have an average diameter of between 0.1 and 10 micrometers, preferably between 0.2 to 5 micrometers, and preferably between 0.5 to 2 micrometers.

The superficial pores of the present invention can be arranged so that the smaller, second pores are within the larger, first pores. The superficial pores of the present invention can extend into the hydrogel substrate preferably no more than 1 millimeter, preferably no more than 500 micrometers, and preferably no more than 200 micrometers. The hydrogel substrate of the present embodiment can be made up of polyvinyl alcohol having a water content of at least 5% and preferably at least 30% w/w of the overall hydrogel.

In one embodiment of the invention, the superficial pores of the substrate described herein can be arranged in a regular repeating fashion. Such a pattern or waffle structure can be used in embodiments of varying pore size as well as in embodiments where the smaller superficial pores are within the area of the larger superficial pores.

A method provided by the present invention of making a hydrogel substrate possessing a textured surface required by the present invention comprises using an extremely accurate etching technology to generate a mold, pouring a liquid solution of the hydrogel into the mold, allowing the liquid hydrogel to polymerize and/or crosslink while in the mold, and removing the solid hydrogel substrate from the mold. The extremely accurate etching technology can be (microelectromechanical systems) MEMS technology or its equivalent. Also, the hydrogel substrate made from this method could be a polyvinyl alcohol hydrogel having a water content of at least 5% and preferably at least 30% w/w of the overall hydrogel.

The present invention also includes a method for making a hydrogel substrate by contacting solid objects with a liquid hydrogel, allowing the hydrogel to polymerize and crosslink while the solid objects are at least partially immersed in the hydrogel, and removing those solid objects from the polymerized and crosslinked hydrogel to form superficial pores therein. The solid objects used to impart the superficial pores may be made of polystyrene beads. Also, the solid objects used to impart the superficial pores may be grit, sand, silicon, silica, and ultra-fine particulate matter. The solid objects used to create the superficial pores can have a diameter of between 3 and 1000 micrometers, preferably between 10 and 300 micrometers, and preferably between 30 and 100 micrometers.

The solid objects used to create the superficial pores of this invention can be removed by use of an organic solvent or other washing means. This hydrogel can be comprised of polyvinyl alcohol possessing a water content of at least 5% w/w of the overall hydrogel.

Accordingly, the present invention is directed to an implantable hydrogel substrate product, a method of making that product, and a method of using that product which substantially improves upon the limitations existing in the art. The invention provides methods of selectively promoting cellular residence and/or differentiation over a surface as described herein. To achieve these and other advantages in accordance with the purpose of the invention, as embodied and broadly described herein, the invention includes a load bearing biocompatible hydrogel for medical implantation that promotes bone attachment. The hydrogel consists of a surface component which has been optimized for implantation. This is accomplished through pores on the surface having a controlled range in distribution of size. The surface pores are superficial and do not extend throughout the hydrogel.

Hydrogels are materials whose state is between that of a solid and of a liquid. Gels consist of polymeric, i.e. long chain, molecules linked together to form a three-dimensional network and are embedded in a liquid medium. In the case of hydrogels, the liquid medium comprises water. The polymer backbone of hydrogels is formed by hydrophilic monomer units and may be neutral or ionic. Examples of neutral and hydrophilic monomer units are ethylene oxide, vinyl alcohol, (meth)acrylamide, N-alkylated (meth)acrylamides, N-methylol(meth)acrylamide, N-vinylamides, N-vinylformamide, N-vinylacetamide, N-vinyl-N-methylacetamide, N-vinyl-N-methylformamide, hydroxyalkyl (meth)acrylates such as hydroxyethylmethacrylate, vinylpyrrolidone, (meth)acrylic esters of polyethylene glycol monoallyl ethers, allyl ethers, of polyethylene glycols, and sugar units such as glucose or galactose. Examples of cationic hydrophilic monomer units are ethyleneimine (in the protonated form), diallyldimethylammonium chloride and trimethylammonium propylmethacrylamide chloride. Examples of anionic monomer units are (meth)acrylic acid, crotonic acid, maleic acid, fumaric acid, itaconic acid, 2-acrylamido-2-methylpropanesulfonic acid, vinylsulfonic acid, vinylphosphonic acid, 2-methacryloyloxyethanesulfonic acid, 4-vinylbenzenesulfonic acid, allylsulfonic acid, vinyltoluenesulfonic acid and vinylbenzenephosphonic acid.

From the example listing above, a hydrogel for use in the present invention may be selected based upon its biocompatibility and stability at various hydration states. For the purposes of the present invention, a suitable hydrogel will have a moisture content of at least 5% w/w of the overall hydrogel, preferably at least 10%, 15%, 20%, 25%, 30%, 35%, 40%, 50%, 60%, 70%, or 80% w/w of the overall hydrogel.

Initial events following implantation of a biomaterial in an orthotopic surgical site include rapid adsorption of serum constituents onto the implant surface. The first cells that are likely to come into contact with the surface are polymorphonuclear cells, platelets, monocytes, and macrophages. These cells release bioactive factors that promote mesenchymal cell migration to the wound site. In addition to these natural factors associated with wound healing, surgeons frequently use bone graft and bone graft substitutes to improve bone formation. Such materials include osteoinductive agents such as demineralized bone matrix and bone morphogenetic protein. If appropriate signals are present mesenchymal cells with an osteoprogenitor phenotype will continue to differentiate into osteoblasts; of these a subset will become osteocytes. Ultimately, the newly formed bone will be remodeled via osteoclastic resorption. The invention provides that physical stimulation of cells via a controllably textured surface contributes to desired cellular differentiation, adhesion, and acceptance of the implant. The present invention also provides that well-known grafting agents may be incorporated into the hydrogel composition, which include, but are not limited to growth factors, angiogenic agents, antibiotics, and the like.

Chemically modified or polar surfaces are generally known to be able to produce more reactive protein adsorption to the implant surface than unmodified or non-polar surfaces. The increased reactivity of the proteins adsorbed onto the polar surface is thought to promote cellular adhesion to that surface. Therefore, the invention provides that the hydrogel composition can possess chemically modified or polar surfaces.

In general, many materials are well-tolerated in bone, but the success of long-term or chronic implantation often depends on the intimacy of the interface between the material surface and the bone. Microarchitecture of the surface is an important determinant of cell response. It has been observed that osteoblast phenotypic expression is surface-dependent. As described herein, specific surface characteristics enhance osteoblast differentiation while permitting proliferation, leading to optimal cell response to the implantation. Likewise, cartilage or cartilage-derivative cells show enhanced differentiation based on surface microarchitecture. Since both bone and cartilage cells are derived from mesenchymal stem cells and have as a common ancestor, osteoprogenitor cells, the present invention refers to bone and bone-like cells to encompass that branch of the differentiation pathway. Stated differently, the present invention provides for the differentiation of bone cells (for example osteocytes, osteoblasts, osteoclasts) as well as bone-like cells (for example chondrocytes or related cartilaginous tissue producing cells).

The mechanical properties of the material must be appropriate for the application. When the mechanical properties of the material are similar to the mechanical properties of the tissue adjacent to the implant, tissue tolerance of the artificial material is enhanced. Polymeric and elastomeric biomaterials can be fabricated with a wide range of mechanical properties, making them suitable for many applications as implantable devices. Because of their high water content, similar to that of living tissue, hydrogels are superior in biocompatibility to non-hydrous polymeric materials. Polyvinyl alcohol (PVA) is an example of a polymer that can be used to form hydrogels, and has been studied extensively for its potential in biomedical applications. Polyvinyl alcohol hydrogels (PVA-Hs) are biologically well tolerated and compatible with living cartilage tissue.

PVA-Hs can be produced from solution via repeated freezing and thawing cycles that increase the order of the microcrystalline regions, changing the dissolution properties, mesh size, and diffusion properties of the polymer. Also, PVA-Hs can be produced from solution via a slow and sustained transition through the freezing point of the solution. The mechanical properties of PVA-Hs can be varied over a wide range, and stable PVA gels can easily be produced to have an elastic modulus ranging from a few MPa, such as articular cartilage, to about 50 MPa, such as the stiffest portion of the annulus of spinal discs. Increasing the stiffness of a hydrogel can also be achieved through chemical crosslinking. Examples of chemical crosslinker groups are vinyl groups, allyl groups, cinnamates, acrylates, diacrylates, oligoacrylates, methacrylates, dimethacrylates, oligomethacrylates, or other biologically acceptable groups.

Increasing the porosity of a hydrogel substrate produces decreased mechanical strength. When porous hydrogels are used to provide the requisite surface of the present invention, it is advantageous that the porosity not extend throughout the hydrogel, but be limited to a relatively shallow depth below the surface. The thickness of the porous portion of the hydrogel is preferably less than 1 millimeter, less than 500 micrometers, and most preferable less than or equal to 200 micrometers.

The porosity of the hydrogel surface embodied in this invention may be realized in a variety of ways. Molds may be constructed with patterning on the appropriate surfaces of the cavities in the mold. Alternatively, the porosity can be produced by abrasion of a smooth hydrogel surface after molding. Abrading the surface can result in a surface textured such as desired in this invention. Techniques for applying and using abrasives are well known to those of skill in the art.

Using extremely accurate surface building or etching techniques, one can generate extremely intricate surfaces to use as a mold for a surface envisioned by the present invention. Solid free-form fabrication methods offer several unique opportunities for the construction of medical devices. Solid free-form fabrication methods can be used to selectively control composition within the build plane by varying the composition of printed material. This means that unconventional microstructures, such as those with complicated porous networks or unusual gradients, can be designed at a computer-aided design (CAD) terminal and built through a solid free-form process such as three-dimensional printing or MEMS microfabrication techniques.

In one embodiment of this invention the molds for casting the hydrogels are created using MEMS micro-fabrication techniques to produce materials with precise repetitive arrays. The microfabrication process uses commercially available, epoxy-based photoresist and standard photolithography masks and techniques to produce the specified surface architecture. The dimensions of features in the x-y plane of the surface are specified by the photomask. The height of the features is dictated by the thickness of the photoresist layer prior to exposure and development. Multiple photoresist layers may be cast and exposed with different masks to build up very complex structures. An example of one such complex feature, with a pseudofractal architecture is shown in the "snowflake" pattern, seen in FIG. 2.

Photolithography is the process of transferring geometric shapes on a mask to the surface of a silicon wafer. The steps involved in the photolithographic process are wafer cleaning; barrier layer formation; photoresist application; soft baking; mask alignment; exposure and development; and hard-baking.

There are two types of photoresist: positive and negative. For positive resists, the resist is exposed with UV light wherever the underlying material is to be removed. In these resists, exposure to the UV light changes the chemical structure of the resist so that it becomes more soluble in the developer. The exposed resist is then washed away by the developer solution, leaving windows of the bare underlying material. The mask, therefore, contains an exact copy of the pattern which is to remain on the wafer.

Negative resists behave in just the opposite manner. Exposure to the UV light causes the negative resist to become polymerized, and more difficult to dissolve. Therefore, the negative resist remains on the surface wherever it is exposed, and the developer solution removes only the unexposed portions. Masks used for negative photoresists, therefore, contain the inverse (or photographic "negative") of the pattern to be transferred.

MEMS fabrication of hydrogel mold surfaces for use in this invention may, for example, involve standard photolithography techniques and epoxy-based photoresists (SU-8 2000 series, MicroChem, Newton, Mass.) in a Class 10 clean room facility. Photolithography masks can be designed, for example, using a CAD program, or its equivalent, and supplied to order (DuPont Photomasks, Inc., Round Rock, Tex.).

One embodiment of this invention is an artificial intevertebral disc, comprising one or more hydrogels shaped substantially similarly to a natural intevertebral disc. The upper and lower surfaces of the hydrogel, or assembly of hydrogels, are constructed to have a textured surface with a defined level of porosity. That porosity depends primarily upon the size and number of the surface features of the mold used to create the surface texture.

Another embodiment of this invention is a substrate used to repair tissue that has been damaged either chronically or acutely. This substrate can be implanted at a damaged area such as knee cartilage, shoulder bursa repair, or other damaged area one skilled in the art would foresee.

FIG. 1 shows a spinal disc replacement envisioned by the present invention. The spinal disc has an upper portion 1 and a lower portion 2. It is the surfaces of the upper portion 1 and lower portion 2 which possess the textured surface envisioned by the present invention. The upper portion 1 and lower portion 2 will be less elastic and more rigid than the inner region 4 which seeks to mimic the nucleus pulposus. Likewise, the spinal disc may have an intermediate region of elasticity 3 which further aids in the function of the spinal disc. The intermediate region of elasticity 3 may or may not differ from the elasticity of either the inner region 4 or the upper portion 1 or lower portion 2.

The size of the pores comprising the textured surface of the hydrogel can aid in promoting adhesion of one cell type over the other. For example, bone cells can show better attachment and results on textured surfaces where the pores are larger than the pores on a textured surface where cartilage cells attach. The ability to promote bone cells to attach to a given surface as compared to cartilage cells can be considered in the design of an implant. For example, a biomedical implanted device which needs a more rigid attachment to the native bone might require the attachment of bone cells as opposed to cartilage cells, requiring using a surface with larger pores. Likewise, a different implant may need to induce cartilage development on the surface of the implant and would instead use the textured surface composed of overall smaller pores to enable that selection. Other factors such as the age, sex, and pre-existing medical condition of the patient would be considered depending upon the circumstances.

Conversely, the present invention provides for a hydrogel substrate that can be implanted which possesses multiple regions on that substrate capable of promoting the differentiation and attachment of both bone and bone-like cells such as, for example, osteocytes and chondrocytes. Such a surface would, after the migration of mesenchymal stem cells, promote the differentiation of the mesenchymal stem cell into the osteoprogenitor cell and ultimately into bone and cartilage cells on each type's respective region. Stated differently, the present invention provides for a single hydrogel substrate that has both bone cell promoting regions and cartilage, or bone-like cell, promoting regions.

Osteoblasts assume distinct morphologies depending on the architectural features of their substrate. On microrough surfaces, as long as the peak-to-peak distance is less than the length of the cell body, the cell bodies become more cuboidal, and anchor themselves to the surface through long dendritic filopodia. In contrast, on smoother surfaces osteoblasts flatten and spread, resulting in a fibroblastic appearance. The cell morphology correlates with the physiological behavior of the cells. On smooth surfaces, prostaglandin synthesis is low, TGF-β1 levels are low, alkaline phosphatase specific activity is low, and osteocalcin levels are low, whereas proliferation rates are relatively high in comparison with cells cultured on rougher surfaces. That is, a greater number of cells may be present on smooth surfaces, but the cells on textured surfaces show greater tendency to proliferate into bone or bone-like cells.

Responsiveness to the surface also depends upon the state of maturation of the cell in the osteoblast lineage. Examinations of numerous cell lines and primary cell cultures from the multipotent fetal rat calvarial cells to the osteocyte cell line MLO-Y4 have occurred. These experiments indicate that as cells become more mature, the stimulatory effect of the microrough surface on differentiation becomes attenuated. It is, however, only on textured surfaces and only in the presence of bone morphogenic protein-2 (BMP-2), that fetal rat calvarial cells are able to establish three dimensional nodules that form mineral in a physiological relevant manner. The results support in vivo observations that a mineral can affect cells directly on the surface as well as distal to the biomaterial indicating that the extracellular signaling factors released by the cells in direct contact with material are sensed by other cells in the microenvironment, and potentially systematically as well.

The surface texture is created by the distribution of pores which do not continue throughout the hydrogel, or stated differently, are superficially located on the hydrogel substrate. These pores can be broken into at least two size groups: large pores and small pores. The large pores can range in size from 3 to 1000 micrometers in diameter. Preferably, the large pores can range in size from 10 to 300 micrometers in diameter. And preferably, the large pores can range in size from 30 to 100 micrometers in diameter. The small pores are smaller in diameter. For example, the small pores can range in size from 0.5 to 20 micrometers in diameter. Preferably, the small pores can range in size from 1 to 10 micrometers. And preferably, the small pores can range in size from 2 to 5 micrometers. The present invention also provides for third, fourth, fifth, and greater numbers of pore sizes on the hydrogel substrate.

Figure 2:
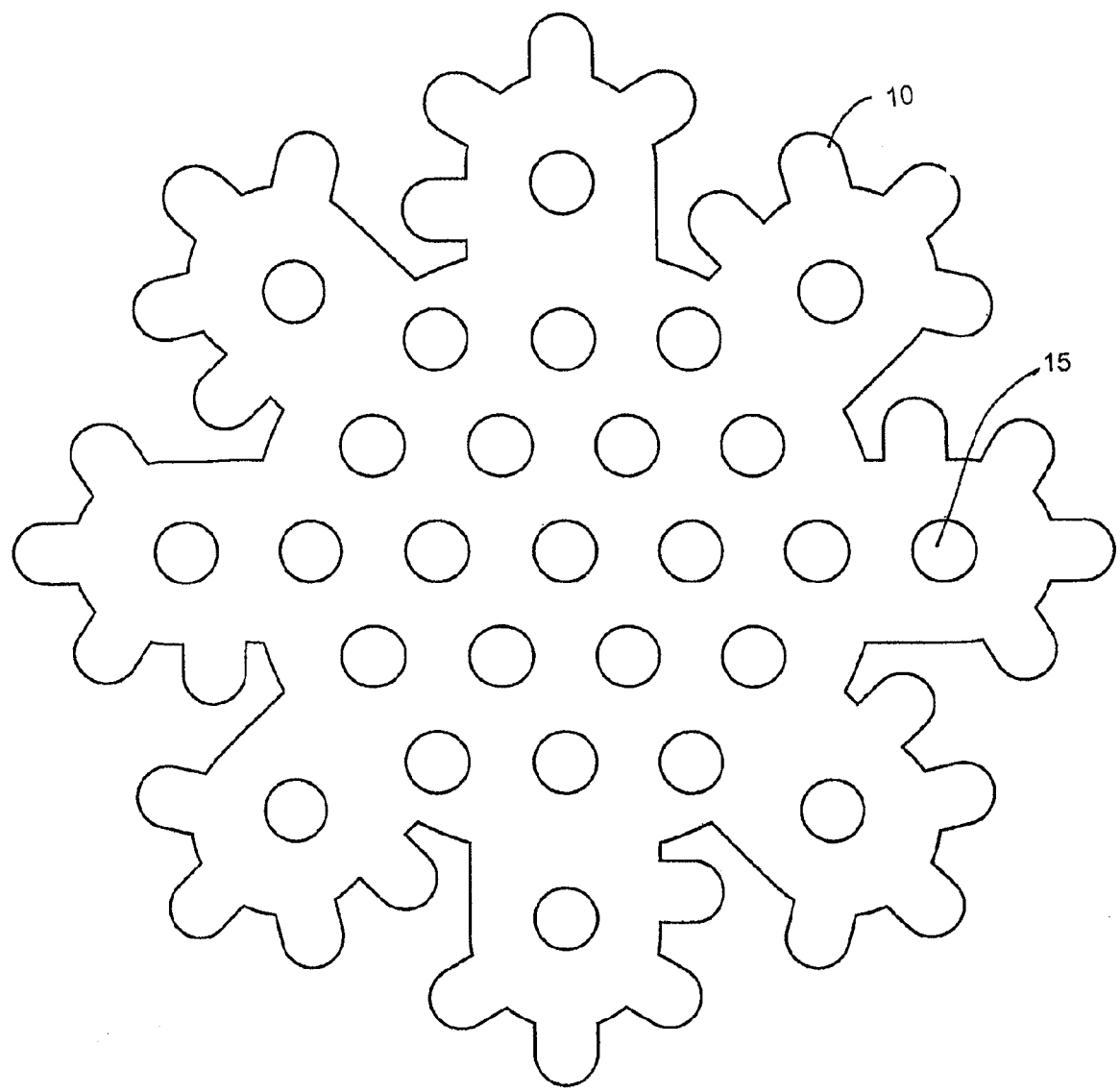
FIG. 2 is an example of a superficial surface pore construct exemplary of one embodiment of the present invention.

FIG. 2 depicts a superficial pore 20 as envisioned by the present invention. The superficial pore contains a large pore 10 and a small pore 15. The small pores 15 are located within the large pore 10. The small pores 15, in this embodiment, are equally spaced from one another by one diameter and are positioned in a hexagonal layout.

The pores on the textured surface in this embodiment enable the surface to resemble native bone which has undergone osteoclastic resorption. Increasing the porosity of a PVA-H generally reduces the mechanical strength of the implant. When surface textured hydrogels are used to provide the requisite surface texture, it is advantageous for the pores not to extend throughout the hydrogel, but instead be limited to a relatively shallow depth below the textured surface. The thickness of the porous portion of the hydrogel is less than 1 millimeter, preferably less than 500 micrometers, and preferably less than or equal to about 200 micrometers.

In order to measure differentiation of cells into bone or bone-like cells four markers are known in the art. The presence of alkaline-phosphatase, TGF-β1, $PGE_2$, and osteocalcin function as reliable indicators of cellular differentiation into bone or bone-like cells. Specifically, it has been shown that MG63 osteoblasts, NHOst cells, and fetal rat calvarial cells will attach to surfaces and then differentiate into secretory osteoblasts that exhibit increased levels of alkaline phosphatase activity and osteocalcin. As surface microroughness increases, levels of $PGE_2$ in the conditioned medium also increase. $PGE_2$ stimulates osteoclastic activity at high levels, but is required to be present at low levels for osteoblastic activity to occur. It has been previously shown that the elevated prostaglandin levels that are seen in cultures grown on rough microtopographies appear to be required for enhanced osteogenesis since inhibition of prostaglandin production by indomethacin blocks the increase in osteoblast phenotypic expression on these substrates.

TGF-β1 levels are also surface dependent. The amount of TGF-β1 produced by osteoblasts cultured on surfaces is modulated in a surface dependent manner by factors that regulate osteogenesis and subsequent bone resorption. Regulation of TGF-β1 is important to bone formation for a number of reasons. This growth factor stimulates proliferation of mesenchymal cells and enhances the production of extracellular matrix, particularly of type 1 collagen.

Osteocalcin is the most abundant non-collagenous protein in bone, comprising almost 2% of total protein in the human body. It is important in bone metabolism and is used as a clinical marker for bone turnover, but its precise function remains elusive. With no known enzyme activity, osteocalcin's function depends on its structure. That structure reveals a negatively charged protein surface that places five calcium ions in positions complementary to those in hydroxyapatite, the structural mineral component of bone. In addition to binding to hydroxyapatite, osteocalcin functions in cell signaling and the recruitment of osteoclasts and osteoblasts, which have active roles in bone resorption and deposition, respectively.

The hydrogels of the present invention may contain bioactive factors to further stimulate cell growth or differentiation. These factors, for instance attachment peptides, such as RGD containing peptides, and growth factors such as bone morphogenic proteins, insulin-like growth factor, platelet derived growth factor, fibroblast growth factor, cartilage-derived growth factor, transforming growth factor-beta, and parathyroid hormone related peptide, as well as other regulatory chemicals such as statins, prostaglandins, and mineral ions are well known in the art. These factors may be included in the hydrogels of this invention singly or in combination, and they may be included with or without their respective binding proteins.

The hydrogels of the present invention may also contain bone or cartilage forming cells (osteoblasts or chondrocytes) or precursor cells to bone and cartilage forming cells such as mesenchymal stem cells or osteoprogenitor cells. These precursor cells have the capacity to differentiate into bone and/or cartilage forming cells. Cells may be included in the hydrogels of the present invention alone or in combination with bioactive factors to further stimulate cell growth or differentiation.

Natural intervertebral discs have a tough outer fibrocartilaginous ring called the annulus fibrosus and a soft, inner, highly elastic structure called the nucleus pulposus. The artificial discs of the present invention may contain an inner core constructed to mimic the physical and mechanical properties of the natural nucleus pulposus, surrounded by an annular region constructed to mimic the physical and mechanical properties of the natural annulus fibrosus.

In one embodiment, these regions comprise hydrogels whose water content, degree of polymerization, and degree of crosslinking are routinely adjusted to produce the requisite physical and mechanical properties. The hydrogel comprising the inner core has a higher water content and/or a lower degree of polymerization and/or a lower degree of crosslinking to produce a relatively soft and elastic hydrogel. The hydrogel comprising the outer annular region has a lower water content and/or a higher degree of polymerization and/or crosslinking to produce a relatively hard outer hydrogel which mechanically is tough and stiff. The hydrogels comprising the upper and lower surfaces may substantially resemble the hydrogel comprising the annular region in terms of physical and mechanical properties, water content, and degrees of crosslinking and polymerization. The additional requirement, however, for the surfaces to be textured may allow or require a different combination of physical and mechanical properties in these hydrogels compared to the hydrogel comprising the outer annular region.

In yet another embodiment of the present invention, the hydrogel substrate can be a load bearing patch which can be used in the repair of partially or predominately damaged tissue. For example, the hydrogel substrate bearing the textured surface of the present invention can be relatively thin and small in diameter. That hydrogel substrate can then be placed where deteriorated, either acutely or chronically, cartilage was removed.

In yet another embodiment of the present invention, the hydrogel substrate can be assembled outside the body in a malleable form. The malleable form of the hydrogel substrate can then be placed in the intended area, be it a spinal disc replacement, knee cartilage replacement, shoulder bursa repair, or other use one skilled in the art would foresee. Once in the proper position, the malleable hydrogel substrate could be hardened or polymerized via photopolymerization. Radiation curing or photopolymerization (photo-induced free radical polymerization) has become an important and useful technique for applying and curing coatings, inks and adhesives. Radiation-curable compositions typically comprise as essential components one or more radiation-curable monomers and a photoinitiator. The compositions are applied as a coating to various articles and surfaces and the monomers are polymerized to form a film by exposing the coating of the radiation-curable composition to radiation, typically ultraviolet (UV) or electron-beam radiation. Examples of chemical crosslinker groups are vinyl groups, allyl groups, cinnamates, acrylates, diacrylates, oligoacrylates, methacrylates, dimethacrylates, oligomethacrylates, or other biologically acceptable photopolymerizable groups.

In yet another embodiment of the present invention, the biocompatible material used in implantation is selected from the group of polymers, ceramics, metallics, organo-metallics, or other known biocompatible materials. To be used as described herein, the materials need to be castable, formed by the use of molds, in order to have rendered upon the surfaces of the materials the necessary forms embodied in this invention. Castable ceramics would be a preferred selection as the materials are often formed in manners which resembled native bone or bone structures. Likewise, biocompatible metallic components could be fashioned using the various embodiments of this invention such to direct cellular attachment and proliferation at the surface of the implant.

EXAMPLES

Example 1

A simple mold surface pattern in accordance with this invention, for example, is an array of cylinders which are 5 μm in diameter and 5 μm in height. To construct a mold surface with this pattern, a 4-inch diameter silicon wafer is coated with a 5 μm thick layer of SU-8 2005 by spin coating at 3000 rpm for about 30 seconds. The wafer is then placed on a hotplate at 65° C. for about 1 minute and then at 95° C. for about 2 minutes. The wafer is then exposed to UV light through a photomask defining the array of cylinders using, for example, a mask aligner (Karl Suss MA-6). The exposure time is calculated to give an exposure energy of 75 mJ/cm at a wavelength of 365 nm. The exposed areas of the photoresist are then crosslinked by heating the wager on a hotplate at 65° C. for about 1 minute and then at 95° C. for about 1 minute. The unexposed areas of the photoresist are then dissolved away by immersing the wafer in solvent (SU-8 Developer, MicroChem, Newton, Mass.) for about 1 minute with continuous gentle agitation. The completed wafer is then rinsed, for example, with isopropyl alcohol and dried in a stream of nitrogen. Profilometry measurements and evaluation by scanning electron microscopy can be used to verify that the desired surface pattern is produced.

Example 2

A more complicated pattern for a hydrogel mold surface, in accordance with the present invention when generated could for example, consist of an array of cylinders 100 μm in diameter and 100 μm in height. Each cylinder is topped with a smaller array of cylinders, 5 μm in diameter, and 5 μm in height. The construction of such a mold requires two layers of photoresist and two separate exposures of those layers. First, a 4-inch diameter silicon wafer is coated with a 100 μm thick layer of SU-8 2050 by spin coating at 1700 rpm for about 30 seconds. The wafer is then placed on a hotplate at 65° C. for about 4 minutes and then at 95° C. for about 1 minute. The wafer is then exposed to UV light through the photomask defining the array of large cylinders, using, for example, a mask aligner (Karl Suss MA-6). The exposure time is calculated to give an exposure energy of 450 mJ/cm$^2$ at a wavelength of 365 nm.

The exposed areas of the photoresist are then cross-linked by heating the wafer on a hotplate at 65° C. for about 1 minute and then at 95° C. for about 9 minutes. Without developing the first layer, the wafer was coated with a 5 μm thick layer of SU-8 2005 by spin coating at 3000 rpm for about 30 seconds. The wafer is then placed on a hotplate at 65° C. for about 1 minute and then at 95° C. for about 2 minutes. The wafer is then exposed to UV light through the photomask defining the array of small cylinders using, for example, a mask aligner (Karl Suss, MA-6). The exposure time is calculated to give an exposure energy of 75 mJ/cm$^2$ at a wavelength of 365 nm. The exposed areas of the photoresist are then crosslinked by heating the wafer on a hotplate at 65° C. for about 1 minute and then at 95° C. for about 1 minute. Finally, the unexposed areas of both photoresist layers are then dissolved away by immersing the wafer in solvent (SU-8 Developer, MicroChem, Newton, Mass.) for about 9 minutes with continuous gentle agitation. The completed wafer is then rinsed with, for example, isopropyl alcohol and dried in a stream of nitrogen. Profilometry measurements and evaluation by scanning electron microscopy can be used to verify that the desired surface pattern has been produced.

Example 3

Figure 3:
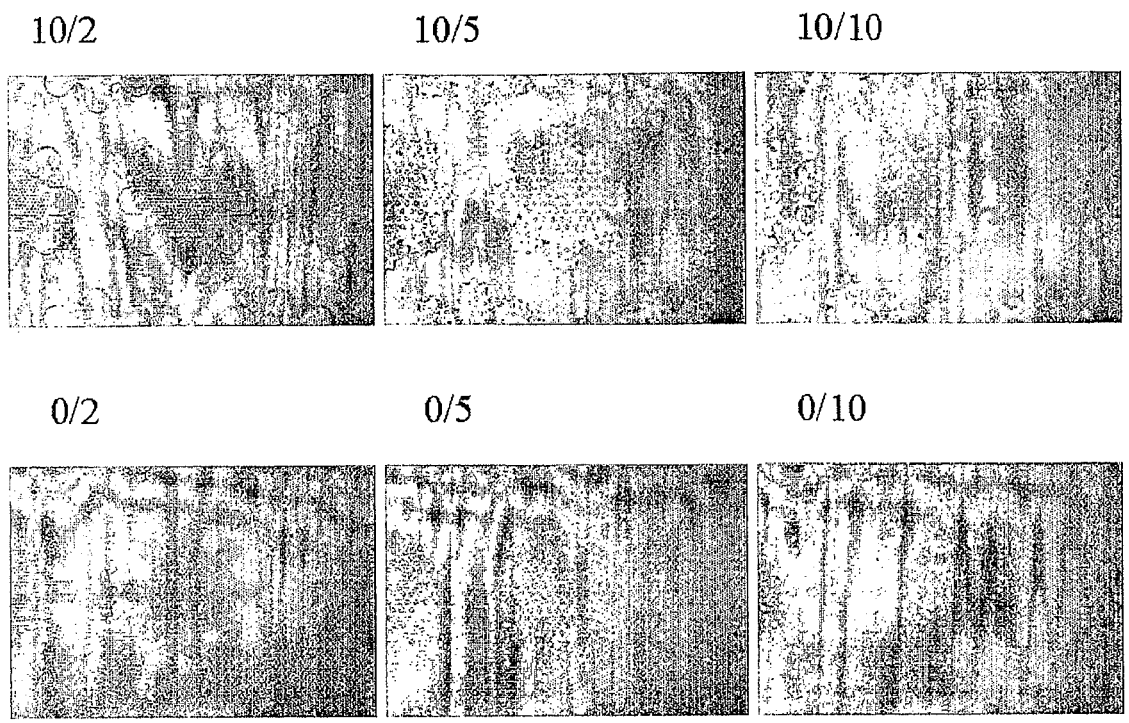
FIG. 3 are multiple types of superficial surface pores embodied by the present invention.

Under the methods of this invention, enhanced differentiation of cells into bone or bone-like cells is seen. Specifically, experiments were run using the PVA-H of this invention in multiple forms. This description references FIGS. 3-5 for clarity. As shown in FIG. 3 there were seven conformations of the surface topography taught by this invention used in this experiment—one being smooth hydrogel. Specifically, conformation is described using a two number nomenclature system such as PVA-H 10/2. PVA-H 10/2 refers first to the size of the large pore on the surface. As described above, the large pore can exist in a complex structure resembling a snowflake. The number 10 in the first position represents a large pore of 100 µm in diameter. The number in the second position of the nomenclature system refers to the size and arrangement of the small pores superimposed on the large pore surface. The second position numbers of 2, 5, and 10 refer to a diameter of 2 µm, 5 µm, and 10 µm, respectively. The spacing and orientation of the small pores on the large pore surface follows a hexagonal grid with a spacing between the small pores of twice the diameter of the small pores.

Moving clockwise through FIG. 3, surfaces are shown possessing a 100 µm large pore with a 2 µm small pore (10/2) 50, a 100 µm large pore with a 5 µm small pore (10/5) 55, a 100 µm large pore with a 10 µm small pore (10/10) 60, no large pore with 10 µm small pores (0/10) 65, no large pore with 5 µm small pores (0/5) 70, and no large pore with 2 µm small pores (0/2) 75. Not shown is smooth PVA-H which would receive the 0/0 designation in the above described nomenclature.

Figure 4:
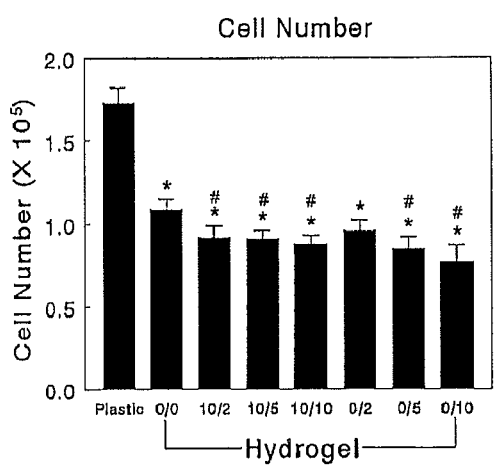
FIG. 4 is a graph of cell proliferation seen on the surfaces of FIG. 3.
Figure 5:
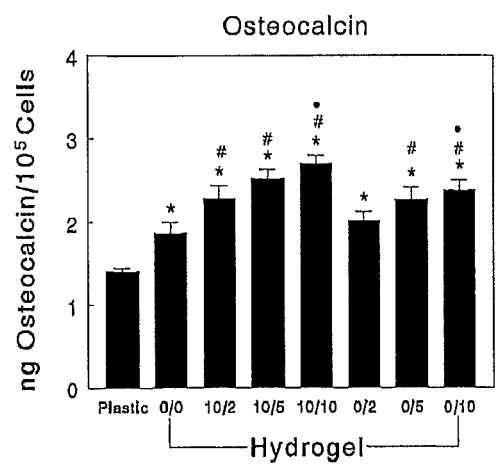
FIG. 5 is a graph of increased bone or bone-like cell markers resulting from exposure to the surfaces of FIG. 3.

FIGS. 4 and 5 when taken together indicate that while tissue culture plastic provides for the greatest amount of cellular proliferation, textured PVA-Hs promote increased differentiation into bone or bone-like cells. MG63 cells were cultured in conditioned media on the surfaces. Specifically, the cells cultured on the 10/10 conformation 60 showed the greatest level of secreted osteocalcin. The next highest amount of osteocalcin secretion was seen in the 10/5 conformation 55. This indicates the enhanced ability to generate differentiation into bone or bone-like cells by the mimicking of native osteoclastic resorption sites on PVA-H by the use of the present invention.

Figure 6:
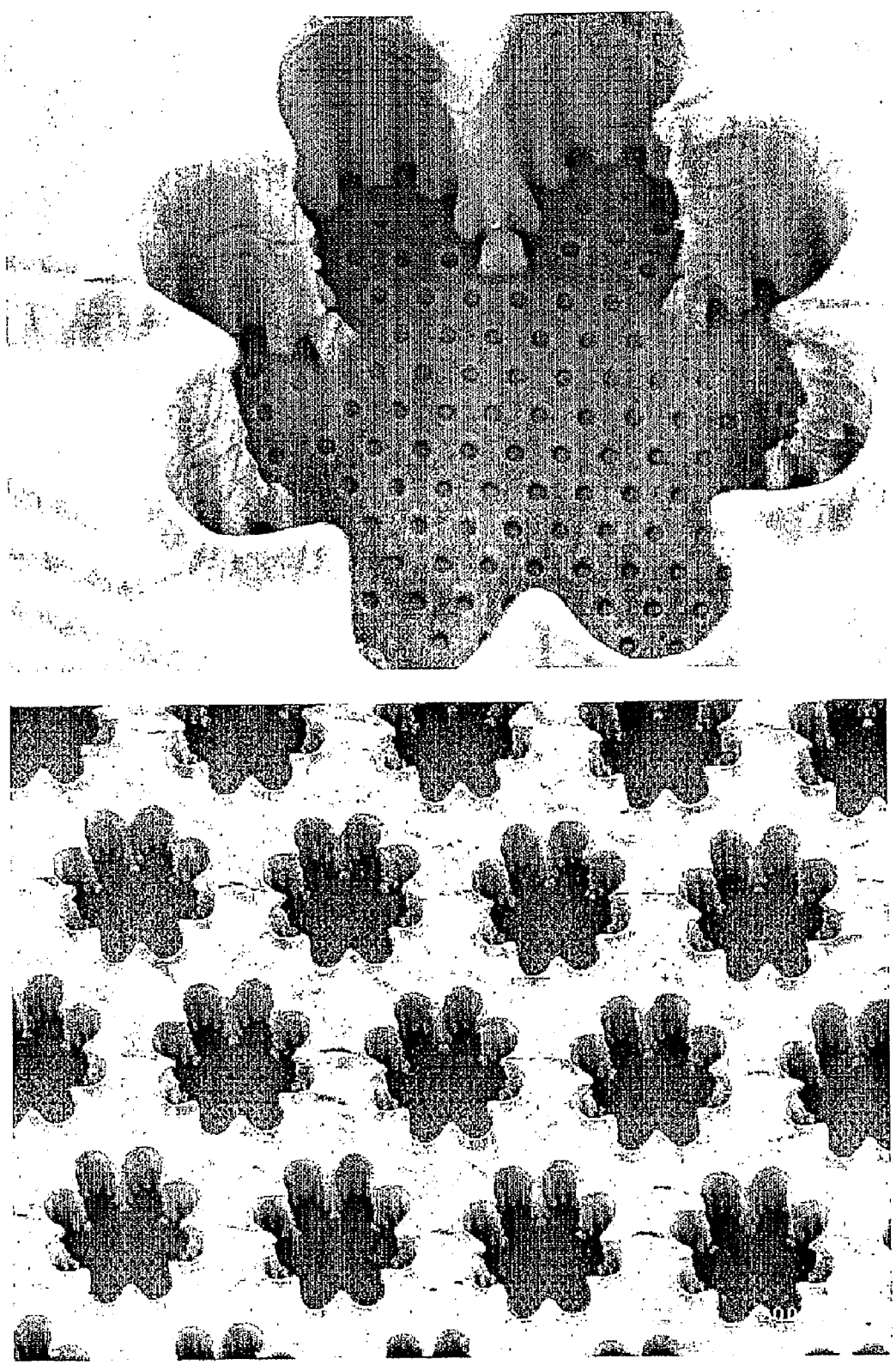
FIG. 6 is an image of a substrate which has been generated in accordance with the present invention. The upper image is a further magnification of the image in the lower portion of FIG. 6.

FIG. 6 is an image of the surface of a substrate manufactured in accordance with the present invention. The image shows the surface of a hydrogel that was cast in a mold similar to those depicted in FIG. 3. It should be noted that the substrate could have been generated with this pattern out of any of the materials described herein. FIG. 6 shows an embodiment of a hydrogel implant having a plurality of smaller pores (or cavities) that extend through a bottom surface of a larger pore (or cavity).

Example 4

Solid polystyrene objects having complex shapes may be fabricated from uniform polystyrene beads by chemically attaching beads of different sizes. This is illustrated by the following example.

To a suspension of carboxyl-modified polystyrene beads (20.3 µm+/−0.43 µm diameter, Bangs Laboratories) in 20 mM MES, pH 4.5 is added a 10-fold excess of water-soluble carbodiimide, 1-Ethyl-3-(3-dimethylaminopropyl) carbodiimide hydrochloride. After 15 minutes at room temperature, the beads are washed twice by centrifugation and suspension in 20 mM HEPES, pH 7.5 and then resuspended in the same buffer. This suspension is added to a stirred suspension of a sufficient amount of amino-modified polystyrene beads (3.10 µm +/−0.06 µm diameter, Bangs Laboratories) to give a 25-fold molar excess of amino groups over carboxyl groups, in the same buffer. After 3 hours at room temperature, the unreacted excess smaller beads are removed. Microscopic examination shows substantially monodisperse particles composed of 20-µm beads having the majority of their surface covered with a single layer of 3-µm beads.

The polystyrene objects of the foregoing example may be used as a template to fabricate a mold for providing the desired porous surface of the hydrogels of the present invention. This may be accomplished by making a metallic replica of a surface comprising a plurality of polystyrene objects using sputtering and/or metal plating techniques and the like, all of which are well known to those skilled in the art. The metallic replica thus produced may be replicated again and reinforced with further metal or other components, again using methods well known to those skilled in the art. The result is a mold suitable for producing the complex surface texture of the hydrogels of the present invention.

Although the invention has been described with reference to a particular preferred embodiment with its constituent parts, features and the like, these are not intended to exhaust all possible arrangements, mechanical and electrical equivalents, or features, and indeed many other modifications and variations will be ascertainable to those of skill in the art.

What is claimed is:

1. A method of making a hydrogel having an outer surface and a plurality of first superficial pores and a plurality of second superficial pores along at least a portion of said outer surface, said method comprising:

providing a mold having an array of first projections and an array of second projections thereon for creating a plurality of first and second pores;

wherein said array of first projections is configured to form the plurality of first pores, each of said first pores being defined by a first cavity extending from the outer surface of the hydrogel to a bottom surface of said first cavity;

wherein said array of second projections extends from an end of at least one of the first projections, said second projections configured to form the plurality of second pores;

wherein each of said second pores is defined by a second cavity extending below the bottom surface of a first cavity;

casting a hydrogel in the mold;

allowing the hydrogel to form while in the mold; and removing the hydrogel from the mold;

wherein said first cavities and said second cavities are only located on or near the outer surface of the hydrogel; and wherein said hydrogel is adapted for long term or chronic implantation such that said hydrogel remains within a joint after implantation to augment cartilage and function as cartilage replacement.

2. The method of claim 1, wherein the providing a mold having first and second projections is accomplished at least partially with microelectromechanical systems (MEMS) technology or its equivalent.

3. The method of claim 1, wherein the hydrogel comprises polyvinyl alcohol.

4. The method of claim 3, wherein the content of said polyvinyl alcohol is at least 30% of the total hydrogel.

5. The method of claim 1, wherein both the first and the second cavities are arranged in a regular repeating fashion.

6. The method of claim 1, wherein the first cavities and second cavities are within 1 millimeter of the outer surface of the hydrogel.

7. The method of claim 1, wherein the first cavities have an average cross-section of between 10 to 300 micrometers, and wherein the second cavities have an average cross-section of between 1 to 10 micrometers.

8. A method of making a substrate configured for use as a load bearing device within an anatomy, said method comprising:

providing a mold having a plurality of first and second projections thereon, said first and second projections corresponding to a plurality of first and second superficial cavities to be formed on or near an outer surface of the substrate;

wherein each of the first projections is configured to form a first cavity along the outer surface of the substrate;

wherein the plurality of second projections extend from at least one of the first projections of the mold, said second projections being configured to form a plurality of second cavities along a bottom surface of at least of the first cavities, each of said second cavities having a cross section that is smaller than a cross-section of the first cavities;

pouring a liquid solution of a hydrogel into the mold;

allowing the hydrogel to polymerize and crosslink while in the mold; and removing the hydrogel from the mold;

wherein the second cavities are located within an area of the first cavities; and wherein said substrate is configured for use as a cartilage replacement device.

9. The method of claim 8, wherein the providing a mold having projections is accomplished at least partially with microelectromechanical systems (MEMS) technology or its equivalent.

10. The method of claim 8, wherein the hydrogel comprises polyvinyl alcohol, and wherein the content of said polyvinyl alcohol is at least 30% of the total hydrogel.

11. The method of claim 8, wherein the first cavities and the second cavities are within 1 millimeter of the outer surface of the substrate.

12. The method of claim 8, wherein the first cavities have an average cross-section of between 10 to 300 micrometers, and wherein the second cavities have an average cross-section of between 1 to 10 micrometers.

* * * * *